United States Patent [19]
Enright et al.

[11] Patent Number: 4,745,915
[45] Date of Patent: May 24, 1988

[54] SURGICAL DRAPE

[75] Inventors: Clarence R. Enright, Grey Eagle; Leland W. Annett, Lake Elmo; David B. Padget, Woodbury, all of Minn.

[73] Assignee: Medical Concepts Development, Inc., St. Paul, Minn.

[21] Appl. No.: 903,443

[22] Filed: Sep. 4, 1986

[51] Int. Cl.⁴ ................... A61B 19/08; A61M 27/00
[52] U.S. Cl. ................................ 128/132 D; 128/171
[58] Field of Search ............... 128/132 R, 132 D, 171, 128/165

[56] References Cited
U.S. PATENT DOCUMENTS

| | | | |
|---|---|---|---|
| 1,554,692 | 9/1925 | Shane | 128/132 D |
| 3,561,440 | 2/1971 | Bayer | 128/132 D |
| 3,968,792 | 7/1976 | Small | 128/132 D |
| 3,989,040 | 11/1976 | Lofgren | 128/132 D |
| 4,169,472 | 10/1979 | Morris | 128/132 D |
| 4,596,244 | 6/1986 | Jackson | 128/132 D |

*Primary Examiner*—Richard J. Johnson
*Attorney, Agent, or Firm*—Lawrence M. Nawrocki

[57] ABSTRACT

A disposable surgical drape (10). It includes a tubular-shaped protective film (14) with a pull-tab (24) which lends itself to remote removal from an adhesive layer (20) on the protective film (14) so that the drape can be secured to a patient (22) without contamination of the incision area. An embodiment of the drape (10) comprises a protective film (14) which, when circumferentially spaced portions thereof are bonded together by, for example, a heat seal (15), defines a channel (16) which can function as a fluid conduit to remove bodily fluids from the surgical incision area.

14 Claims, 2 Drawing Sheets

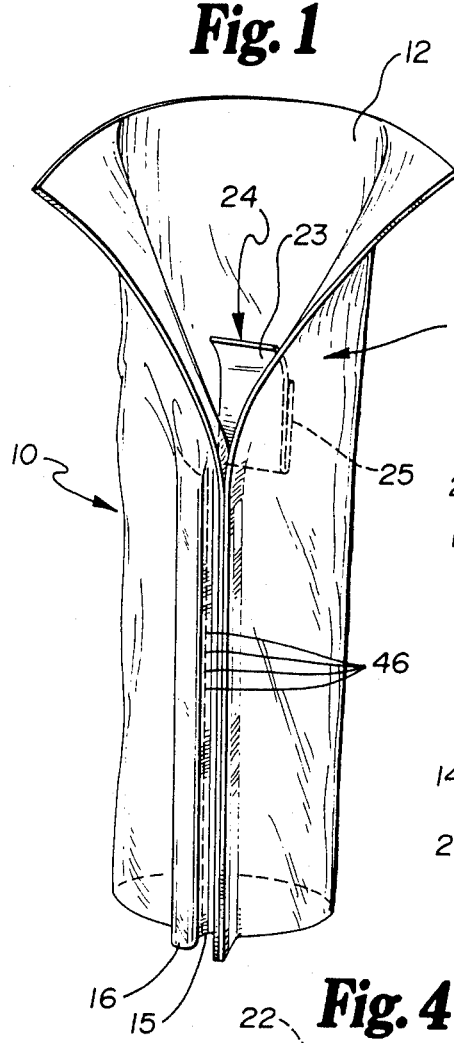
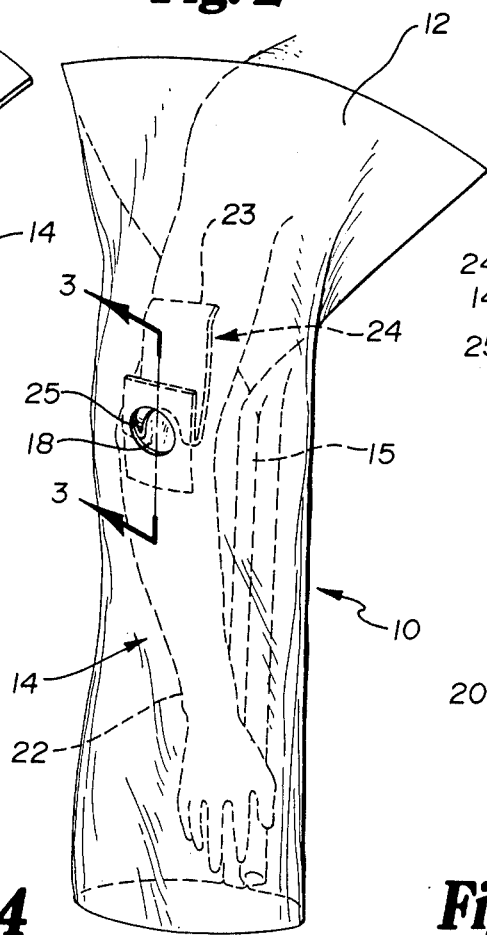
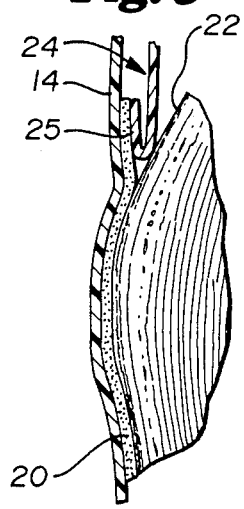
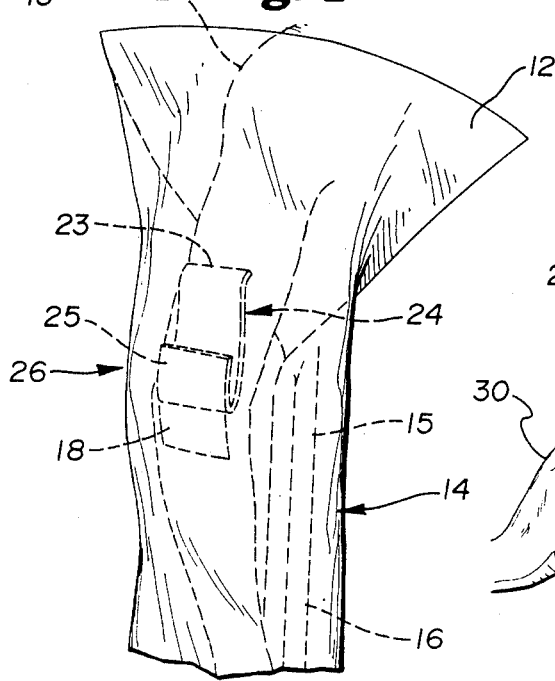
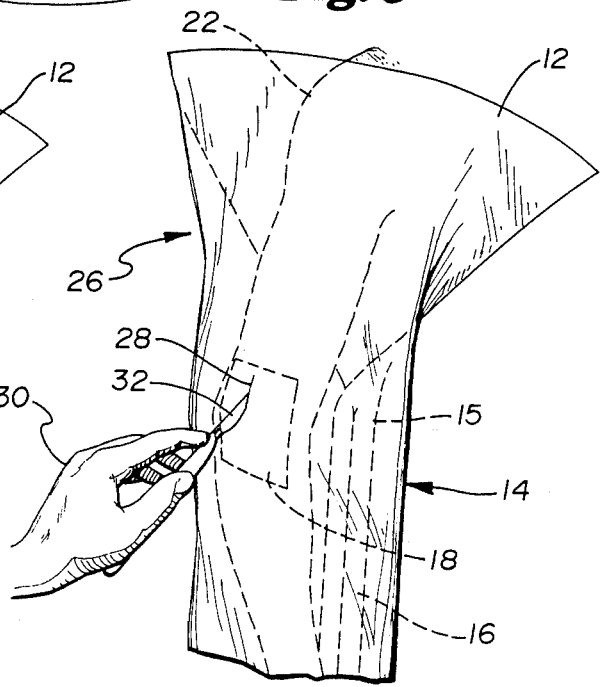

SURGICAL DRAPE

TECHNICAL FIELD

This invention is generally related to the field of devices to prevent contamination of an incision area during a surgical procedure. The invention more specifically, however, relates to a disposable surgical drape with a pull-tab, having a portion overlying an adhesive surrounding a window in the drape, of a length to enable remote removal of the portion overlying the adhesive surface proximate the window, so that the drape can be secured to the patient's body without contamination.

BACKGROUND OF THE INVENTION

Surgical drapes made of cloth have been in use for a number of years. These cloth surgical drapes are reusable, however they require laundering and careful sterilization after previously being used.

The heavy weight of cloth drapes can cause the drape to slide, if imbalanced, away from the incision area. The size and weight of cloth surgical drapes can make them difficult to position and to secure in position once it is attained. This tendency of a cloth drape to slip from its position and the requirement for means for fastening the drape to the patient's body are distinct disadvantages of such a drape. Additionally, significant expense can be involved in sterilization.

Disposable surgical drapes have also been employed and are known in the prior art. Because they are disposable, the need for sterilization after use is obviated. The need remains, of course, for the maintaining of their sterility prior to their use.

Disposable surgical drapes have been difficult to maintain in place due to a lack of weight. As a result, the drape might be permitted to slip away from the incision area. The area is, thereby, exposed to contamination. Use of heavier disposable drapes would help minimize this problem, however they would decrease the economic advantages associated with disposability.

The introduction of adhesive backing to disposable drapes has helped to eliminate the slippage problem. Prior art devices employ peel-off paper backing for exposing the adhesive on the under-side of the surgical drape to the patient's body.

A problem with the prior adhesive backed disposable surgical drapes has been the potential for contamination which results from the need for human intervention to peel off the paper backing. Contamination of the surgical site can occur during the taking of this action.

Positioning of adhesive on the surgical drape is important. Where the disposable surgical drape has the adhesive, peel-off backing in the center of the drape, optimal use cannot be made of the drape. Application of the adhesive substance to the periphery of a window formed in the surgical drape allows for the secure positioning of the drape with the window at the incision area.

In the prior art, drainage troughs were employed for removal of bodily fluids from the incision area. Such removal was effected by osmosis and interior tubing in combination with a suction device.

Prior surgical drapery has, primarily, been flat sheets of either cloth or paper. When the incision area has been on a patient's limb, the drape material was arranged as well as it could be around the generally cylindrical body limb.

Another problem in the prior art is providing the ability to convey bodily fluids secreted at the incision area away from that area as quickly and as sanitarily as possible. Absent adequate provision for conveying means, such fluids tend to saturate the area and provide a growth medium for bacteriologicial growth.

The present invention addresses these problems associated with the prior art and provides for a new and improved tubular-shaped, disposable surgical drape with a pull-tab covered adhesive for securing the drape to the patient's body. Additionally, it provides a conduit for removal of bodily fluids from the incision area.

SUMMARY OF THE INVENTION

The present invention is a surgical drape for deterring contamination of the incision area during a surgical procedure. It includes a protective film for covering the patient's body or anatomical portion during the surgical procedure, means for adhering the film to the patient's body, and means for remotely exposing the adhering means to permit securing the protective film to the patient at a desired location without contamination of the sterilized incision area.

The protective film can be formed into a tubular shape for ease in draping a patient's limb. Additionally, the tubular-shaped drape can be flared at one end for ease in fitting it to the patient's torso adjacent the limb to be operated upon.

A window is formed in the protective film for exposing a body part to be operated upon; for example, when a knee is to receive orthoscopic surgery. Adhesive is carried by a side of the drape, encircling the window to allow for the securing of the drape to the body part. A pull-tab can be peeled off the adhesive to expose the adhesive. This permits for the facile positioning of the drape prior to it being secured to the patient's body.

The pull-tab can comprise an adhesive protective portion which is withdrawn from around the window from a position remote from the incision area to allow for the exposure of the adhering means. After the pull-tab is withdrawn, the adhering means encircling the window can be engaged with the patient's skin at the incision area and pressed down to maintain the drape at the desired location.

In a preferred embodiment, the tubular drape can be constructed so that a bodily fluid disposal channel is integrally formed therein. Two circumferentially spaced portions of the wall of the drape can be fused together by heat sealing one portion to another. The channels thereby created can be disparate in size, a smaller of the channels functioning as a fluid conducting conduit.

The seam formed by the heat sealing process insulates each of the channels from each other. A perforated line can be formed in the seam so that, if desired, the bodily fluid conveying channel can be diverted from the drape proper.

A pouch or pouches can also be provided and can be configured for disposition proximate the window in the drape so that bodily fluids secreted from the incision will flow into the pouch or pouches. If desired, means can be provided for establishing fluid communication between the pouch or pouches and the fluid disposal channel formed integrally in the drape.

Various advantages and features of novelty which characterize the invention are pointed out with particularlity in the claims annexed hereto and forming a part hereof. However, for a better understanding of the invention, its advantages, and objects attained by its use, reference should be had to the drawing which forms a further part hereof, and to the accompanying descriptive matter, in which there are illustrated and described certain embodiments of the invention.

BRIEF DESCRIPTION OF THE DRAWINGS

FIG. 1 is a perspective view of a surgical drape in accordance with the present invention;

FIG. 2 is a perspective view of the surgical drape of FIG. 1 drawn over a patient's limb with the adhesive area around the window within the drape being partially exposed to the patient's limb;

FIG. 3 is a sectional view taken generally along the line of 3—3 of FIG. 2;

FIG. 4 is a perspective view of a second embodiment of the present invention wherein no window is formed in the drape;

FIG. 5 is a perspective view of the embodiment of FIG. 4 illustrating the surgeon using a scalpel to incise the drape and make entry to the patient's body;

DETAILED DESCRIPTION OF THE INVENTION

Figure 6:
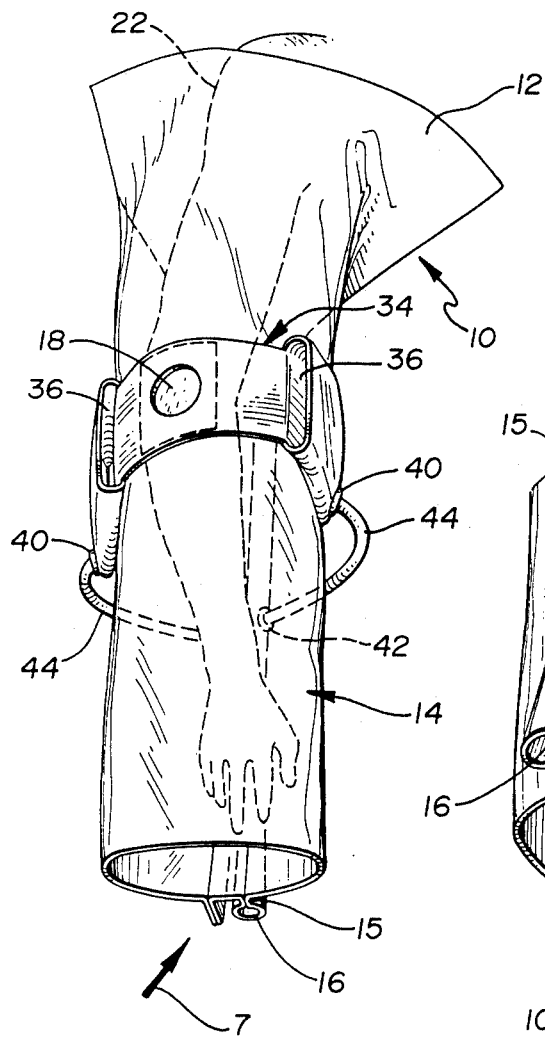
FIG. 6 is a perspective view of the embodiment of FIG. 1 illustrating the drape in use in combination with a saddlebag-type pouch arrangement.

Referring now to the drawings wherein like reference numerals denote like elements throughout the several views, FIG. 1 generally illustrates a disposable surgical drape 10 in accordance with the present invention. The drape 10 is in tubular form.

The drape 10 has an unsealed flared end 12 to facilitate fitting around a patient's limb at the joinder of the limb to the patient's torso. Such fitting is illustrated in FIGS. 2, 4, 5 and 6.

The drape 10 comprises a protective film 14. By means of heat sealing, a seam 15 is formed to define a channel 16. Channel 16, with the addition of a drain or a pump(not shown) can be used to remove fluid from the area at which incision is to be made.

The tubular shape of the instant invention allows for the fitting of the drape to the individual patient's limb 22, which is shown in phantom in FIGS. 2, 4, 5 and 6. FIG. 2 illustrates the drape with a window aperture 18 formed therein. Window aperture 18 provides access to the proposed incision area.

Adhesive, seen in cross-section in FIG. 3, is a layer 20 of any appropriate substance applied to the inside of the protective film 14. Adhesive layer 20 functions to facilitate application of the surgical drape 10 with the window 18 formed therein to the specific location of the patient's body desired. Adhesive layer 20 permits the surgical drape 10 to be securely positioned and maintained in position during the surgical procedure without the necessity of skin clamps or sutures or other fastening means.

Adhesive layer 20 can be exposed to the patient's limb 22, without the risk of contamination, by withdrawing a pull-tab 24 of a length sufficient to enable removal from a position overlying adhesive layer 20, from a location remote from the surgical site. FIG. 2 illustrates the application of the surgical drape 10 to the patient's body part 22 with the pull-tab 24 being removed to, thereby, expose the adhesive layer 20.

As seen in the figures, and particularly FIG. 1, the pull-tab 24 has a protective portion 25 which overlies adhesive layer 20 surrounding window 18, and a tab portion 23 which is folded back on the protective portion 25 and extends toward the flared end 12 of the surgical drape 10. The distal end of the tab portion 23 projects, in its normal position, beyond an edge of the protective portion 25 most closely proximate the flared end 12 of the drape 10.

As can be seen in view of this disclosure, after the drape 10 is maneuvered so that the patien's limb 22 is in position therewithin, a nurse can reach into the drape 10 from the flared end 12 and grab the protruding tab portion 23 of the pull-tab 24. Because of the disposition of the tab portion 23, his or her hand will never achieve a position immediately proximate the window 18. Consequently, the immediate incision area will not become contaminated by any bacteria associated with the nurse's hand. The pull-tab 24 can, thereafter, be drawn to remove it from the area around the window 18.

FIGS. 4 and 5 illustrate a second embodiment of the invention. Illustrated is a tubular shaped drape 26 which has no aperture therein, although a transparent window 18 can be provided. The surgical drape 26 of this embodiment functions, therefore, as an incise drape; that is, the incision is made through the drape material itself.

In FIGS. 4 and 5, as in FIG. 2, the patient body 22 part is shown in phantom encased within the tubular drape 26. The pull-tab 24 is withdrawn from the drape 26 in the same way as in the original embodiment to thereby expose the adhesive layer 20 to the patient's limb 22. Since the transparent window 18 would, most likely, have adhesive applied over its full under-surface, the protective portion 25 of pull-tab 24 would, therefore, be continuous to cover the full window 18. FIG. 5 illustrates the drape 26 in place with the adhesive layer 20 adhering the drape to the patient's body 22 to stabilize the drape 26 and maintain it in position. FIG. 5 also illustrates the surgeon's hand 30 holding scalpel 32 and making incision 28 through the drape 26.

FIG. 6 illustrates a surgical drape showing a flared tubular-shaped surgical drape 10 with a window aperture 18 formed therein. FIG. 6 also illustrates a saddlebag-type structure 34 having a pair of pouches 36, one at each of opposite ends thereof. When the assembly 34 is straddling the draped limb 22, these pouches 36 receive fluids as they drain from the incision area.

The pouches 36 can collect the fluids or, in conjunction with tubing 44 which communicates through tap fittings 40 with the pouches 36, and through fittings 42 with channel 16, act as a conduit to remove fluids. In this manner, fluids can be drained from the surgical site through the pouches 36 and the associated tubing 44 to the channel 16, and thus away from the surgical site for disposal.

Figure 7:
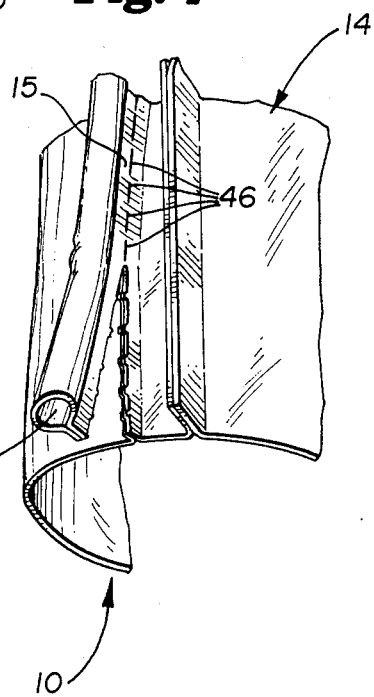
FIG. 7 is an enlarged perspective view from the direction indicated by arrow 7 in FIG. 6.

FIG. 7 is an enlarged view illustrating the channel 16 and heat seal 15. The channel 16 is shown partially separated from the protective film 14 along a line of perforations 46 formed within the heat seal 15 defining channel 16.

Numerous characteristics and advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The invention's scope is, of course, defined in the language in which the appended claims are expressed.

What is claimed is:

1. A drape for preventing contamination of an incision area during a surgical procedure, comprising:
   (a) a protective film for covering a patient's body during a surgical procedure, said film having a window formed therein;
   (b) means, proximate said window, for adhering said protective film to the patient's body with said window overlying the incision area; and
   (c) an elongated pull-tab for exposing said adhering means to the patient's body for securing said protective film thereto, said pull-tab extending, initially, toward, and overlying said window, and thereafter back upon itself to dispose a distal end thereof remote from said window;
   (d) wherein said adhering means is exposed by manipulating said pull-tab remote from said window.

2. The apparatus of claim 1, wherein said protective film further comprises means defining a channel functioning as a fluid conduit for carrying body fluids away from the incision area.

3. The apparatus of claim 1, wherein said protective film further comprises a tubular-shaped drape for covering a patient's limb.

4. The apparatus of claim 3, wherein said tubular-shaped drape includes a flared end for fitting said drape to the patient's body at the torso.

5. The apparatus of claim 1, wherein said protective film is tubular in shape and can be draped over a limb of a patient during a surgical procedure, said film having an aperture therein to provide access to the incision area.

6. A drape for preventing contamination of an incision area during a surgical procedure, comprising:
   (a) a tubular-shaped protective film for encircling a patient's limb during a surgical procedure, said film having a window formed therein;
   (b) means, proximate said window, for adhering said protective film to said patient with said window overlying the incision area;
   (c) an elongated pull-tab for exposing said adhering means to the patient's body for securing said protective film thereto, said pull-tab extending initially toward, and overlying said window, and thereafter back upon itself to dispose a distal end thereof remote from said window; and
   (d) means for removing bodily fluids from the incision area.

7. The apparatus of claim 6, wherein said means for removing said bodily fluids comprises a channel, formed integrally within said protective film, for conducting fluids away from the incision area, said channel being segregatable from the rest of said film.

8. The apparatus of claim 7 wherein said means for removing bodily fluids further comprises at least one pouch disposed relative to said window to receive, at a location remote from the incision area, bodily fluids secreted at the incision area.

9. The apparatus of claim 8 further comprising a length of flexible tubing connecting said pouch to said channel formed within said tubular shaped film, to convey bodily fluids from said pouch and away from the incision area.

10. The apparatus of claim 7 wherein said protective film is heat sealed to define a seam between said channel and the space into which the patient's limb is inserted, and wherein said seam is provided with a multiplicity of perforations to enable said channel to be segregated from the rest of said film.

11. A surgical drape for preventing contamination of an incision area during a surgical procedure, comprising:
   (a) a tubular-shaped protective film, said film having a window formed therein;
   (b) means defining a channel within said film;
   (c) means, proximate said window, for adhering said tubular-shaped protective film to a patient with said window overlying the incision area;
   (d) a pull-tab overlying said adhering means for exposing said adhering means remotely from said window, said pull-tab extending, intially, toward, and overlying said window, and thereafter back upon itself to dispose a distal end thereof remote from said window;
   (e) a pouch disposed relative to said window to receive, at a location remote from the incision area, bodily fluids secreted at the incision area; and
   (f) means for affording fluid communication between said pouch and said channel to effect removal of bodily fluids from the incision area.

12. A drape to inhibit contamination of an incision area on a limb of a patient upon whom a surgical procedure is performed, comprising:
   (a) a protective film encircling the limb substantially along the length of the limb, and having a window formed therein at a location at which said window can be brought to overly the intended incision area, said film having a flared end to accommodate an end of the limb at which it is mated to the patient's torso, and a tapered end to accommodate an end of the limb remote from the patient's torso;
   (b) a layer of adhesive applied to a portion of an inner surface of said film at least surrounding said window; and (c) a pull tab having a protective portion overlying said layer of adhesive, and a tab portion folded back on said protective portion and extending toward said flared end of said film so as to project, in a direction toward said flared end, beyond an edge of said protective portion most proximate said flared end of said film.

13. A drape for preventing contamination of an incision area during a surgical procedure, comprising;
   (a) a tubular-shaped protective film for encircling a patient's limb during a surgical procedure, said film having a window formed therein;
   (b) means for adhering said protective film to said patient with said window overlying the incision area;
   (c) means defining a channel, formed integrally within said protective film, for conducting fluids away from the incision area, said channel being segregatable from the rest of said film;
   (d) at least one pouch disposed relative to said window to receive, at a location remote from the incision area, bodily fluids secreted at the incision area; and
   (e) a length of flexible tubing connecting said pouch to said channel formed within said tubular shaped film, to convey bodily fluids from said pouch and away from the incision area.

14. A drape for preventing contamination of an incision area during a surgical procedure, comprising: (a) a tubular-shaped protective film for encircling the patient's limb during a surgical procedure, said film having a window formed therein;
  (b) means for adhering said protective film to said patient with said window overlying the incision area; and
  (c) means defining a channel, formed integrally within said protective film, for conducting fluids away from the incision area;
  (d) wherein said protective film is heat sealed to define a seam between a channel defined by said channel defining means and the space into which the patient's limb is inserted, and wherein said seam is provided with a multiplicity of perforations to enable the channel to be segregated from the rest of said film.

* * * * *